United States Patent [19]

Afonso et al.

[11] Patent Number: 5,459,146
[45] Date of Patent: Oct. 17, 1995

[54] 4-SUBSTITUTED PYRAZOLOQUINOLINE DERIVATIVES

[75] Inventors: Adriano Afonso, West Caldwell; Joseph M. Kelly, Parlin; Samuel Chackalamannil, East Brunswick, all of N.J.

[73] Assignee: Schering Corporation, Kenilworth, N.J.

[21] Appl. No.: 164,238

[22] Filed: Dec. 9, 1993

[51] Int. Cl.$^6$ .................. A61K 31/47; A61K 31/475; C07D 471/06
[52] U.S. Cl. ............................. 514/292; 546/82
[58] Field of Search ............................. 546/82; 514/292

[56] References Cited

U.S. PATENT DOCUMENTS 3,234,142  2/1966  Wolfrum .................. 252/301.26
3,790,573  2/1974  Blackburn .................. 544/250

FOREIGN PATENT DOCUMENTS 235167   9/1981  Czechoslovakia .
233445   7/1984  Czechoslovakia .
235176   7/1984  Czechoslovakia .
235168   9/1984  Czechoslovakia .
252341   1/1987  Czechoslovakia .
252340   1/1987  Czechoslovakia .
1152341  8/1963  Germany .

OTHER PUBLICATIONS

Ning, "Intromolecular Nitrene . . . ", *J. Org Chem*, vol. 42, No. 10, pp. 1791–1794, 1977, Dec. 1976.
Radl, "Synthesis of Some . . . ", *Coll of Czech Chem Comm*, 50(9), pp. 2010–2014, 1988.
Crenshaw et al, Journal of Medicinal Chemistry, 1976, vol. 19, No. 2, pp. 262–275.
Czechoslovak 34(3–4) pp. 119–122, (1985) and English translation thereof.
Stein et al, Jan. 1970, vol. (13) (1), pp. 153–155. J. Med. Chem.
BIOSIS/CAS Selects: Antiviral Agents Issue, No. 5, 108:55961t, 1988.
Collection Czech. Chem. Commun. (vol. 53) (1988), pp. 1812–1819.
Czech Pharmacy 429–432, (1984), vol. 33(10).
Chem Abstracts 756g vol. 61 of Belgium 632,758, published Oct. 21, 1963.
BIOSIS/CAS Selects Antiviral Agents Issue No. 6, (1989), 110:75486m.
CA2945 f abstract of Ger. 1,152,421, 1964.

Primary Examiner—C. Warren Ivy
Assistant Examiner—D. Margaret M. Mach
Attorney, Agent, or Firm—Eric S. Dicker; John J. Maitner; Matthew Boxer

[57] ABSTRACT

Compounds of the formulas I and II

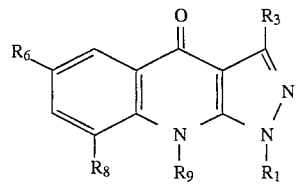

I

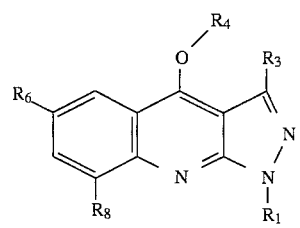

II and pharmaceutically acceptable salts thereof, wherein $R_1$, $R_3$, $R_4$, $R_6$, $R_8$, and $R_9$ are as set forth herein, are described. These compounds are useful as agents for treating patients afflicted with a herpes group virus. Certain of these compounds are also useful as antitumor agents.

11 Claims, No Drawings

4-SUBSTITUTED PYRAZOLOQUINOLINE DERIVATIVES

BACKGROUND OF THE INVENTION

This invention relates to 4-substituted 3-alkyl-pyrazolo[3,4-b] quinoline compounds, pharmaceutical compositions containing them and methods of treating patients afflicted with a herpes group virus infection by use of such compositions.

There are four separate herpes group viruses which infect and cause disease in humans. These four viruses are (1) the herpes simplex virus types 1 and 2 (HSV-1 and HSV-2, respectively); (2) the cytomegalovirus (CMV); (3) varicella-zoster (VZ) virus; and (4) the Epstein-Barr (EB) virus.

Examples of diseases associated with HSV-1 and HSV-2 infections include herpes labialis, genital herpes (herpes progenitalis), neonatal herpes, herpetic keratitis, eczema herpecticum, disseminated herpes, occupational herpes, herpetic gingivostomatitis, meningitis (aseptic), and encephalitis.

The VZ virus is associated with chicken-pox (varicella) and shingles (zoster) in humans.

The CMV is wide spread in humans and numerous other mammals. A great majority of human CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus.

A great majority of serious cases due to CMV infections come from recurring infections in immuno-compromised individuals, such as in transplant patients and in cancer patients. It has been estimated that silent CMV infections have occurred in a majority of humans be the time adulthood is reached.

Examples of drugs used to treat herpes infections include: (1) IUDR (5'-iodo-2'-deoxyuridine); (2) Ara-C (1-[beta-D-arabinofuranosyl] -cytosine); (3) Ara-A (9-beta-D-arabinofuranosyladenine); and (4) Acyclovir (9-[(2-hydroxyethoxy)methyl] guanine). Also Haines et al. (U.S. Pat. No. 4,757,088 issued Jul. 12, 1988) discloses that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of panthothenic acid or its alcohol and salt forms, dexpanthenol and pantothenate, respectively, to lidocaine or lidocaine hydrochloride significantly enhances and antiviral activity of those drugs.

There is still a need for antiviral compounds exhibiting activity against the herpes group viruses, especially against HSV-1 and HSV-2.

SUMMARY OF THE INVENTION

The present invention provides compounds represented by formulas 1a and 1b

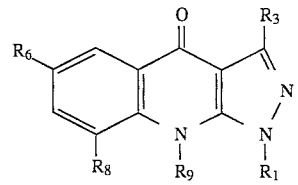

I

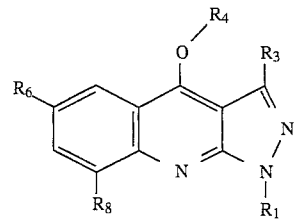

II and pharmaceutically acceptable salts thereof, wherein $R_1$ and $R_9$ each is independently H, $(C_1-C_8)$alkyl, $(C_1-C_8)$alkanoyl, $(C_1-C_5)$alkanoyloxymethyl, benzyloxycarbonyl, $(C_2-C_8)$alkenyl, or $(C_1-C_8)$hydroxyalkyl;

$R_3$ is H or $(C_1-C_3)$alkyl;

$R_4$ is H or $(C_1-C_5)$alkanoyl or $-(CH_2)_2-NR_{4a}R_{4b}$ where each $R_{4a}$ and $R_{4b}$ is independently H or $(C_1-C_8)$alkyl or $R_{4a}$ and $R_{4b}$ taken together are

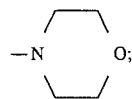

wherein $R_6$ and $R_8$ each is independently H, $-O-(C_1-C_8)$alkanoyl, $-(C_1-C_8)$alkoxy, $(C_2-C_8)$alkenyloxy, halogen, or $(C_1-C_8)$alkyl;

with the proviso that when $R_1$ is H or $-CH_3$, $R_6$ is H or $-OCH_3$, and $R_9$ is H; then $R_3$ cannot be $-CH_3$ and with the further proviso that when $R_4$ is $(C_1-C_8)$alkyl then $R_1$ must be H.

Preferred are compounds of the formulas I and II wherein wherein $R_3$ is $-CH_3$. Also preferred are compounds of the formula II wherein $R_3$ is $-CH_3$. More preferred are compounds of the formula II wherein $R_1$ is H, $R_3$ is $-CH_3$, $R_4$ is $-(CH_2)_2-NR_{4a}R_{4b}$, $R_{4a}$ and $R_{4b}$ are $-CH_3$ and $R_6$ is $-(C_1-C_8)$alkoxy.

Exemplary of compounds of the invention are the following:

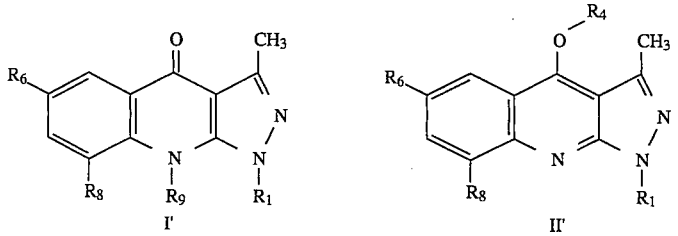

| Compound, Formula | $R_6$ | $R_8$ | $R_4$ when Formula II', $R_9$ when Formula I' | $R_1$ |
|---|---|---|---|---|
| A, II' | $OCOCH_3$ | H | $COCH_3$ | H |
| B, II' | $OCOCH_3$ | H | H | $COCH_3$ |
| C, II' | $OCOC_4H_9$ | H | $COC_4H_9$ | H |
| D, II' | $OCOC_2H_5$ | H | $COC_2H_5$ | H |
| E, II' | $OCH_3$ | H | H | $COCH_3$ |
| F, II' | Cl | H | H | $COCH_3$ |
| G, II' | F | H | $COCH_3$ | H |
| H, II' | F | H | H | $COCH_3$ |
| I, II' | $OCH_3$ | H | $COCH_3$ | $C_7H_{15}$ |
| J, II' | $CH_3$ | H | H | $COCH_3$ |
| K, I' | $OCH_3$ | $CH_3$ | H | $COCH_3$ |
| L, I' | $CH_3$ | H | H | $C_7H_{15}$ |
| M, II' | $CH_3$ | H | $COCH_3$ | $C_7H_{15}$ |
| N, II' | H | $OCH_3$ | H | $COCH_3$ |
| O, II' | $OCH_3$ | H | $-CH_2CH_2N(CH_3)_2$ | H |
| P, II' | $OCH_3$ | H | $CH_3$ | $-(CH_2)_3OH$ |
| Q, II' | $OCH_3$ | H | $-(CH_2)_2$-N-morpholino | H |
| R, II' | $OCH_2CH=CH_2$ | H | H | $-CH_2CH=CH_2$ |
| S, II' | $OCH_3$ | H | H | $C_7H_{15}$ |
| T, I' | H | $OCH_3$ | $-CH_2CH_2-O-CO-C(CH_3)_3$ | H |
| U, II' | H | $OCH_3$ | H | $-CH_2CH_2-O-CO-C(CH_3)_3$ |
| V, I' | H | $OCH_3$ | $-CO-C(CH_3)_3$ | H |
| W, II' | $OCH_3$ | H | H | $-CO-O-CH_2-C_6H_5$ |
| X, I' | $OCH_2CH=CH_2$ | H | $CH_2CH=CH_2$ | $CH_2CH=CH_2$ |
| NN, II' | $OCH_3$ | H | $CH_3$ | H |

The most preferred compound of the invention is:

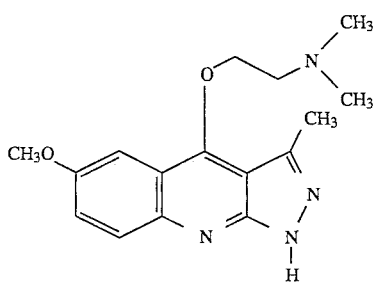

or a pharmaceutically effective salt thereof.

The present invention also provides pharmaceutical compositions for treating patients afflicted with a herpes group virus which comprises an anti-herpes effective amount of a compound of formulas I or II and a pharmaceutically acceptable carrier therefor as well as methods of treating a patient afflicted with a herpes group virus which comprises administering to said patient an anti-herpes effective amount of a compound of formulas I or II.

Certain compounds of the invention are also active as agents in the treatment of tumors. Therefore, the present invention also provides pharmaceutical compositions which comprise certain compounds of the invention, and which compositions are useful for treating patients afflicted tumors. The present invention also provides methods of treating a patient having tumors, which methods comprise administering to said patient an anti-tumor effective amount of certain compounds of the invention.

DETAILED DESCRIPTION OF THE INVENTION

The term "$(C_1-C_8)$alkyl" refers to straight and branched chain hydrocarbon groups of 1 to 8 carbon atoms, such as methyl, ethyl, n-, and iso-propyl, n-, sec- and tert-butyl, n-, sec-, iso-, tert- and neo-pentyl, n-, sec-, iso-, tert-hexyl and n-, sec-, iso-, tert-, and neo-heptyl and n-, sec-, iso-, ten-, and neo-octyl. The preferred $(C_1-C_8)$alkyl is methyl. Alternatively, alkyl with lower numbers of carbon atoms are also referred to in the specification. For example, the term "$(C_1-C_3)$alkyl" refers to straight and branched chain hydrocarbon groups of 1 to 3 carbon atoms, such as methyl, ethyl, n-, and iso-propyl.

The term "$(C_1-C_8)$ alkanoyl" refers to straight and branched chain alkanoyl groups having 1 to 8 carbon atoms such as formyl, acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, octanoyl, 2-ethylhexanoyl and the like. Acetyl is preferred.

The term "$(C_2-C_8)$ alkenyl" refers to straight and branched chain alkenyl groups of 2 to 8 carbons including —$C_2H_3$—, —$C_3H_5$ —$C(CH_3)$ $CH_2$, —$C_4H_7$, and $C_6H_{11}$.

The term "$(C_2-C_8)$ alkenyloxy" refers to alkenyloxy groups of 2 to 8 carbons wherein alkenyl is as described above.

The term "$(C_1-C_5)$ alkanoyloxymethyl" refers to a $(C_1-C_5)$ alkanoyl as described above which is bonded to the rest of the molecule by an —$OCH_2$— moiety.

The term "$(C_1-C_8)$ hydroxyalkyl" refers alkyl groups of 1 to 8 carbon atoms wherein one or more of the hydrogens is replaced by a hydroxy.

The term "halogen" refers to chlorine, fluorine, bromine, and iodine.

The term "$(C_1-C_8)$ alkoxy" refers to straight and branched chain alkoxy of 1 to 8 carbon atoms, such as methoxy, ethoxy, tert-butoxy and the like.

As used herein, compounds of formula II wherein $R_4$ is H, and the compounds of formula I wherein $R_9$ is H, are to be understood as including the tautomeric keto- form. Thus, for example,

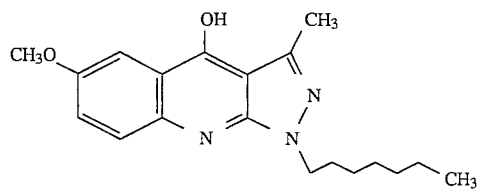

includes the tautomeric keto- form,

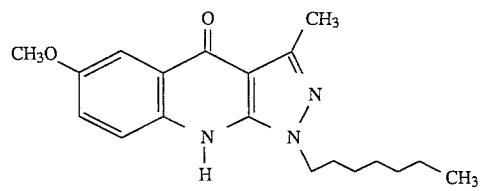

The term "pharmaceutically acceptable salt" refers to maleates, hydrochlorides, hydrobromides, sulfates, phosphates and tartrates. On skilled in the art will realize that acid addition salts of the compounds of the invention may be made with such salts whenever a basic functionality is present in a particular compound of the invention.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of formulas I and II of the present invention may be prepared by analogy to the examples given herein.

The compounds of this invention exhibit anti-HSV activity in two art recognized in vitro assays: (1) a beta Galactosidase Assay and (2) a Plaque Reduction Assay. $IC_{50}$ values for the compounds of this invention in each assay were in the range of 1.0 to <10 µg/mL.

Certain compounds of this invention also exhibit activity in the α-actin assay set forth just below.

IN-VITRO ASSAYS

α-Actin Assay or Anti-tumor α-actin Assay Using Stable Cell Lines

Stable Rat-2 cell lines (Rat-2 Y2) expressing β-galactosidase activity under the control of human α-actin promoter were transformed by ras oncogene. These transformed cells (Y2-HO6), in which the β-galactosidase activity is repressed, were used to identify compounds that have potential anti-tumor activity. Cultured Y2-HO6 cells were seeded onto 96-well assay plates at a density of $1\times10^4$ cells/well. Next day, test compounds were diluted in cell culture media to generate a range of concentrations spanning two logs. After six days of incubation to allow the drugs to affect expression of the reporter—gene, the level of β-galactosidase was measured. The concentration range in which the compound of interest produces significantly higher β-galactosidase activity over the control cells, was reported.

Transient Transfection Assay Systems

In this assay system, the plasmid DNA, containing human α-actin promoter linked to bacterial chloramphemicol acetyl transferase (CAT) reporter-glue, was transfected into ras oncogene transformed into ras oncogene transformed Rat-2 cells (Rat-2 HO6). Following incubation for 6 hours with the transfecting DNA, the cells were washed twice with phosphate buffered saline (PBS) and a fresh medium containing an appropriate concentration of the compound was added. The cells were incubated with the compound for 60 hours, rinsed with PBS twice and collected by scraping the cells in 1 me of PBS. The cell pellet was collected by centrifugation, lysed by suspending in an appropriate buffer and subjecting to the freeze/thaw cycles. The cleared supernatants were used for CAT enzymatic assay using $^{14}$C-labeled chloramphenicol and acetyl coenzyme A as substrate. Equal amounts of protein were taken in the control and drug treated samples for CAT assay. After 30 minute incubation at 37° C., the acetylated chloramphemical was separated from the labeled chloramphenicol by using silca gel based thin layer chromatography. The TLC plates were developed using a chloroform: methanol (95:5) mixture of solvents and exposing to X-ray films. The radioactive spots corresponding to acetylated chloramphemical were out and counted in a scintillation counter. The increase in α-actin promoter driven CAT activity in drug treated sampler versus control was reported.

The compound toxicity assay (3H-LEU), Plaque Reduction Assay for HSV Antiviral Activity (Plaque), and Transient Expression Assay for Effects Against HSV Early Gene Expression (β Galactosidase Assay or βgal) were carried out as set forth in U.S. Pat. No. 5,175,151 which is hereby incorporated by reference.

Test results for compounds of the invention in the above assays are reported below.

| Compound | βgal µg/ml | Plaque µg/ml | $^3$H-LEU µg/ml | α-actin µM range |
|---|---|---|---|---|
| A | 3 | | 14 | 6.25–0.025 |
| B | 8 | | 15 | N.A. |
| C | 5 | | 5 | N.A. |
| D | 11 | | | 50–12.5 |
| E | 3 | | 23 | N.A. |
| F | 9 | | 37 | |
| G | 3 | | 43 | 0.4–0.05 |
| H | 2 | | 32 | N.A. |
| I | 2.8 | | <1 | N.A. |
| J | 9 | | 100 | 500–250 |
| K | 5 | | >100 | 500–250 |
| L | 3 | | 3.4 | N.A. |
| M | 3 | | <1 | N.A. |
| N | 3 | | 100 | N.A. |
| O | 1.4 | 0.7 | 5.4 | |
| P | 7.20 | >20 | | |
| Q | 20 | 20 | | |
| R | 20 | 20 | | |

As used herein N.A. means not active. A blank space indicates that the compound was not tested in the assay.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax. etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be convened, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an antiviral effective amount of a compound of this invention for such mode. The dosages may be varied depending upon the requirements of the patient in the judgment of the attending clinician, the severity of the condition being treated and the particular compound employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses rangling from about 0.1 mg/kg to abut 100 mg/kg of body weight.

The dosage to be administered and the route of administration depends upon the particular compound used, the age and general health of the patient and the severity of the viral condition. Thus, the dose ultimately decided upon must be left to the judgment of a trained health-care practitioner.

As noted above, certain compounds of the invention are also active as anti-tumor agents. These compounds may be administered by any conventional mode of administration by employing an antitumor effective amount of a compound of the invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

EXAMPLES

Example 1

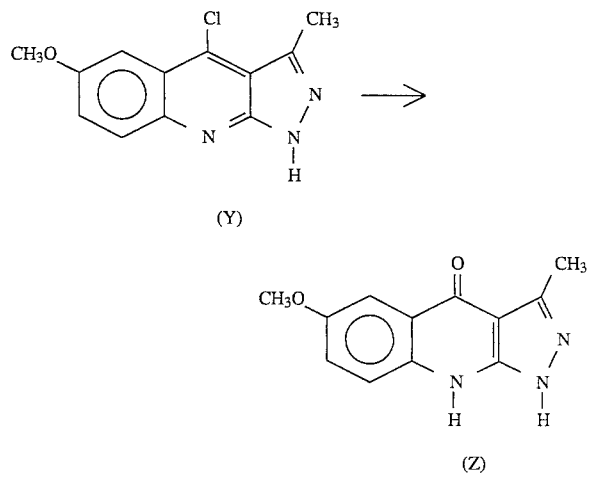

Chloro compound (Y) (11 g, 0.044 mole) was stirred in methanol (100 ml) and 1 normal hydrochloric acid (150 ml) at reflux temperature overnight. The reaction mixture was then cooled, concentrated to about 300 ml and cooled further to 0° C. over ice-bath.

The crystallized solid was filtered, washed with water (20 ml) and dried at 60° C./0.2 mm (10.0 g, 97.2% yield).

The preparation of the starting material, chloro compound (Y), is described in copending U.S. patent application No. 08/164,178 which is hereby incorporated by reference.

Example 2

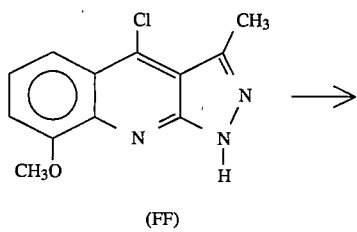

(FF)

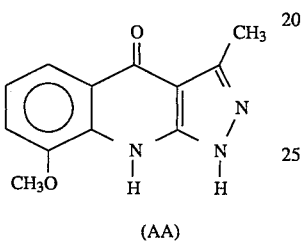

(AA)

white powder (1.0 g) MS EI (M$^+$: 229)

The starting material, chloro compound (FF), is prepared in a manner analogous to the preparation of compound (Y). As pointed out above, the preparation of compound (Y) is described in copending U.S. patent application No. 08/164,178 which is hereby incorporated by reference.

Example 3

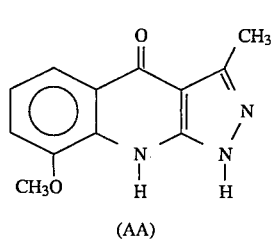

(AA)

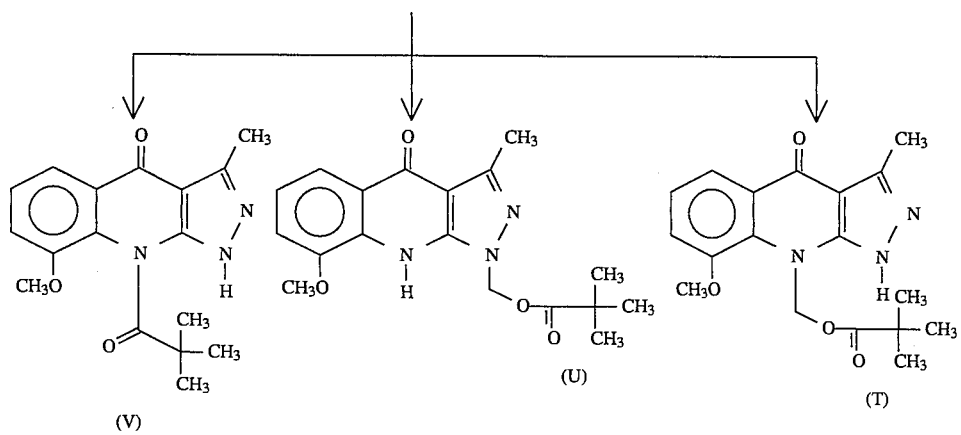

The chloride (1.5 g. 6.07 mmol) was stirred in methanol (50 ml) at 20° C., then 1 normal hydrochloric acid (10 ml) was added. The reaction mixture was refluxed overnight, then cooled and concentrated to 20 ml. Water (20 ml) was added, a solid precipitated, and this solid was filtered, and washed with water (20 ml), and then dried at 60° C./0.2 mm. This solid was chromatographed on silica gel eluting with 4% (V/V) methanol: methylene chloride, and yielded the product which recrystallized from acetone/hexanes as a Sodium hydride 60% in oil (40 mg, 1.0 mmol) was added to a suspension of (AA) (200 mg 0.873 mmol) in tetrahydrofuran (anhydrous 10 mml) and dimethyformamide (anhydrous 10 ml). Chloromethyl pivalate (0.5 ml, 3–46 mmol) was added and the reaction mixture was stirred overnight at 20° C. The solvent was evaporated and the residue was extracted with methylene chloride (50 ml), washed with water (25 ml), dried over magnesium sulfate, and the solvent was evaporated. The residue was chromatographed on silica gel eluting with 20% (v/v) ethyl acetate: hexanes yielding 3 products. Compound T (MS (CI, M$^+$1; 344)), Compound U (MS (CI, M$^+$1;344)), Compound V (MS: (CI, M$^+$1 314)).

Example 4

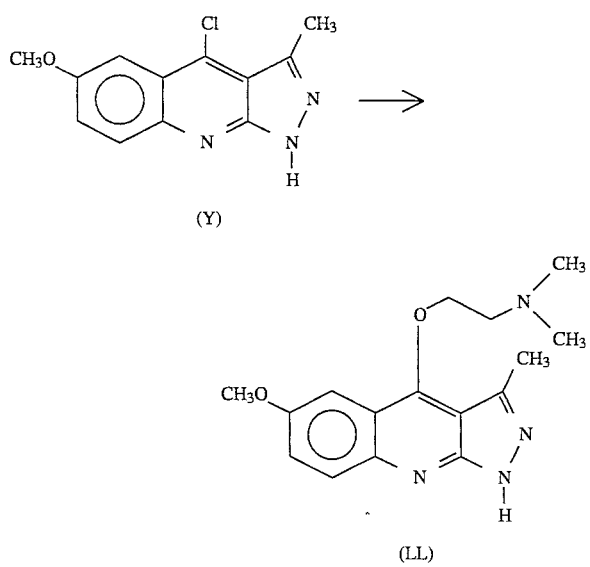

(Y)

(LL)

Sodium hydride 60% in oil, (1.2 g; 4.8 mmol) was added to N,N-dimethylethanolamine (25 ml, 248 mmol), then stirred for 10 minutes. The compound (Y) was added and the resulting mixture was stirred at 110°–120° C. overnight, and cooled to 20° C. Water (80 ml) was added and the mixture was then extracted with methylene chloride (4×100 ml). The organic layer was dried over magnesium sulfate, filtered and evaporated yielding an oily solid, which on trituration with hexanes yielded the product as a pale yellow solid. The solid was chromatographed on silica gel eluting with 5% (v/v) methanol/methylene chloride, and recrystallized from acetone/methylene chloride to yield the product as pale yellow needles. MS EI (M+,272)

Example 5

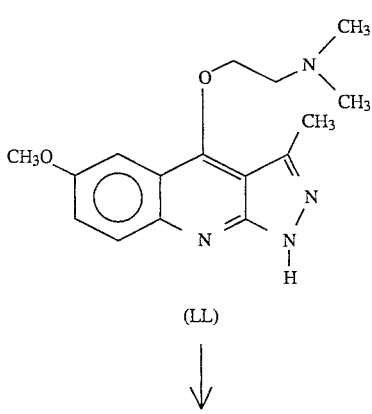

(LL)

↓

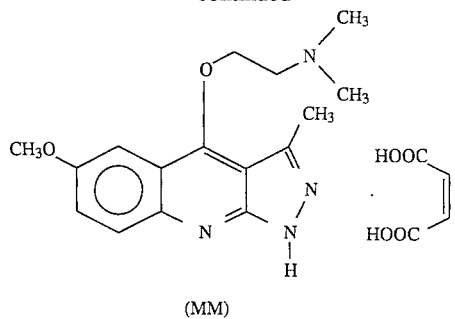

(MM)

Maleic acid (38 mg; 3.27×10$^{-4}$M) was added to a solution of compound, (LL), (100 mg, 3.33×10$^{-4}$M) in methanol (3 ml), then stirred for 5 minutes.

Ether (5 ml) and then methanol (2 ml) were added and the mixture was filtered. Yellow solid precipitated, and was washed with ether (3×10 ml), dried at 60° C./0.2 mm to obtain 100 mg of the title compound.

Example 6

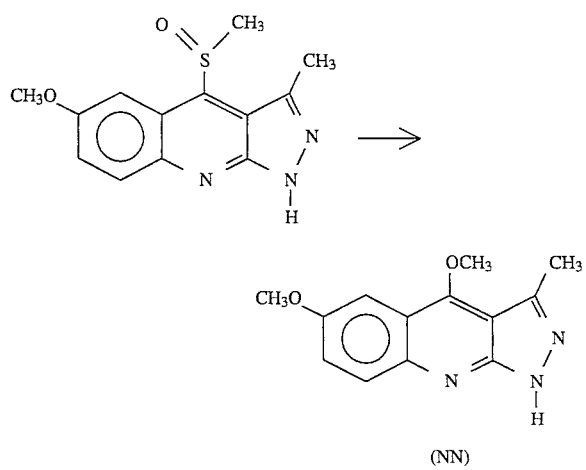

(NN)

Sodium methoxide (3.2 g, 59.7 mmol) was added to a suspension of the sulfoxide (Preparation described Example 7; Patent IN00II —Thiosubstituted pyrazoquinolines) 5.5 g, 19.92 mmol) in methanol (400 ml) were then refluxed for 2½ hours. The reaction mixture was cooled to 20° C., the solvent, was evaporated, the residue was triturated with water (25 ml) and filtered. The solid was washed with water (20 ml) dried at 60° C./0.2 mm, chromatographed on silica gel eluting with 2% v/v methanol methylene chloride yielding the product as a pale yellow powder 4.0 g, 90.9% yield.

MS EI (M$^+$243)

The preparation of the sulfoxide which is the starting material for this example, is described in copending U.S. patent application No. 08/164,178.

Example 7

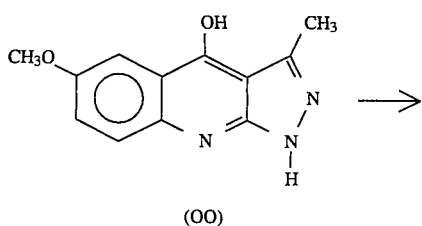

(OO)

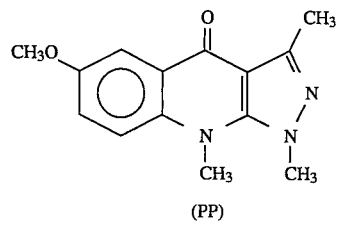

(PP)

Sodium hydride (60% in oil) (3.67 g, 9.19×10⁻²M) was added to a solution of the pyrazoloquinoline, (OO), (8.5 g, 3.67×10⁻²M in 100 ml of anhydrous dimethylformamide (DMF), at 20° C., then stirred 30 minutes. Iodomethane (10 ml, 16.06×10⁻²M) was added dropwise. The reaction temperature rose to 60° C. during the addition. The reaction mixture was stirred overnight at 20° C., then water (200 ml) was added and the solid precipitated. The solid then was filtered, washed with water (100 ml) and then chromatographed on silica gel eluting with 2% methanol/methylene chloride (v/v) yielding the product as white solid.

M.P. 191°–192° C. CI m/e (258,M⁺1)

Compound (O) may be prepared by analogy to the processes set forth in the examples herein.

Example 8

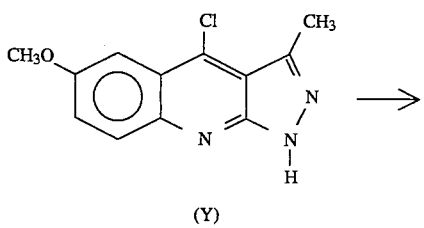

(Y)

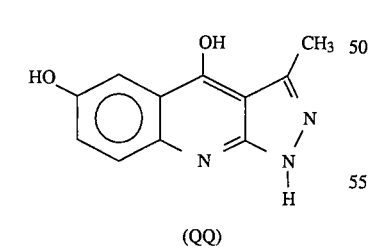

(QQ)

Compound (Y) (22 g, 89 mmol) was stirred in 48% hydrobromic acid at reflux overnight then cooled to 20° C. The crystallized yellow solid, was filtered and washed with water (20 ml). The yellow solid was stirred in 10% saturated sodium bicarbonate (100 ml), and the product was filtered as an off-white solid, (17 g. 88% yield) MS (EI) M+217.

The preparation of the chloride compound, (Y), has been described above.

Example 9

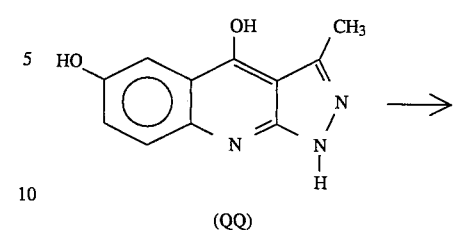

(QQ)

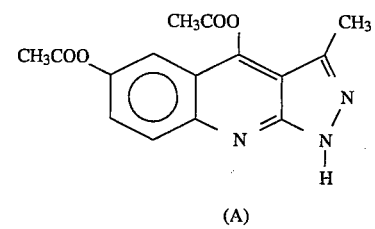

(A)

Triethylamine (15 ml, 0.106 mole) was added to suspension of (QQ) (15 g, 0.69 mole), and pyridine (anhydrous, 200 ml) at 20° C., then acetic anhydride (30 ml, 0.318 mole) was added. Solution occurred, then after 5 minutes, a precipitate appeared. The reaction mixture was stirred 30 minutes, then the yellow precipitate was filtered and washed with water. The solid was suspended in acetone: ether (200 ml, 1:4) and refiltered yielding the product (A) as yellow powder which was dried at 60° C./0.2 mm.

(6.2 g, 30.0% yield) mp. 254°–256° C.

MS CI (M⁺1, 300)

The following compounds were prepared in an analogous manner except that the appropriate acylating agent was used instead of acetic anhydride.:

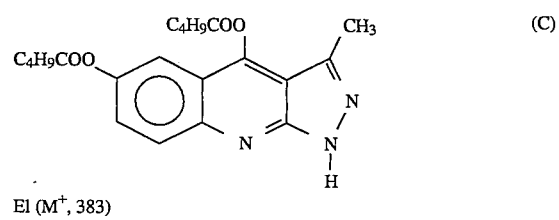

EI (M⁺, 383)

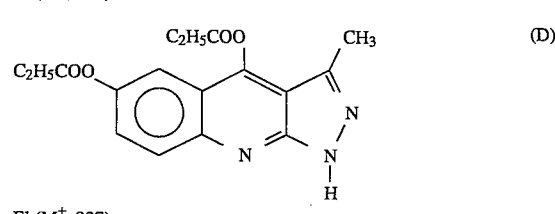

EI (M⁺, 327)

and

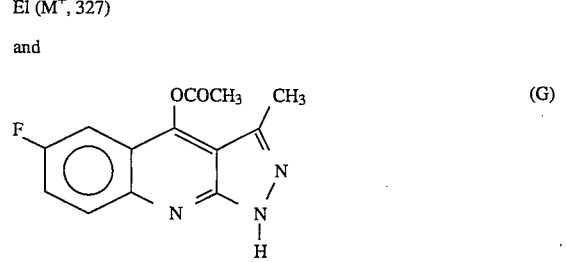

EI (M⁺, 259)

By an analogous process to the one shown in the example just above, the following compounds were made:

(L) [structure] MS EI (M⁺, 369)

and (M) [structure] MS EI (M⁺, 353)

EXAMPLE 10

(QQ) [structure] →

(B) [structure]

Para toluene sulfonic acid monohydrate (10 mg, 0.05 mmol) was added to a suspension of compound (QQ) (300 mg. 1.38 mmol) in acetic anhydride (10 ml) then stirred at reflux for 30 minutes. When solution occurred the reaction was cooled to room temperature. The precipitated white powder was filtered, washed with acetic anhydride (2×5 ml) and water (10 ml) dried at 60° C./0.2 mm, to yield 350 mg of the title compound, MS (EI, M⁺, 299).

By an analogous process to the one shown in the example just above, the following compounds were made:

(F) [structure] MS EI (M⁺, 275)

-continued (J) [structure] MS EI (M⁺, 255)

(K) [structure] MS EI (M⁺, 285)

(H) [structure] MS EI (M⁺, 259)

and (N) [structure] MS EI (M⁺, 271)

Specific compounds of the invention were made by the processes of the examples set forth below, or by processes analogous to the examples set forth below.

| Compounds | Example Number |
| --- | --- |
| A, C, D, G, I and M | 9 |
| B, E, F, H, J, K and N | 10 |
| L, P, R, S, W, and X | 7 |
| NN | 6 |
| O and Q | 5 |
| T, U, and V | 3 |

What is claimed is:

1. A compound of the formula I or II

I

[structure with $R_3$, $R_6$, $R_8$, $R_9$, $R_1$]

-continued

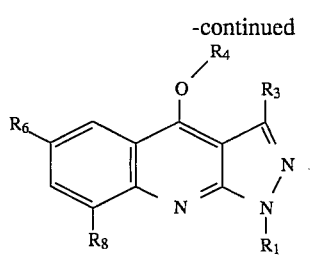

or a pharmaceutically acceptable salt thereof,
wherein $R_1$ and $R_9$ each is independently H, $(C_1-C_8)$alkyl, $(C_1-C_8)$alkanoyl, $(C_1-C_5)$alkanoyloxymethyl, benzyloxycarbonyl, $(C_2-C_8)$alkenyl, or $(C_1-C_8)$hydroxyalkyl;

$R_3$ is $(C_1-C_3)$alkyl;

$R_4$ is H or $(C_1-C_5)$alkanoyl or $-(CH_2)_2-NR_{4a}R_{4b}$ where each $R_{4a}$ and $R_{4b}$ is independently H or $(C_1-C_8)$alkyl or $R_{4a}$ and $R_{4b}$ taken together are

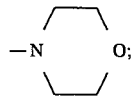

wherein $R_6$ and $R_8$ each is independently H, $-O-(C_1-C_8)$alkanoyl, $-(C_1-C_8)$alkoxy, $(C_2-C_8)$alkenyloxy, halogen, or $(C_1-C_8)$alkyl;

with the proviso that when $R_1$ is H or $-CH_3$, $R_6$ is H or $-OCH_3$, and $R_9$ is H or $-CH_3$, then $R_3$ cannot be $-CH_3$;

and with the further proviso that when $R_4$ is $(C_1-C_8)$alkyl then $R_1$ must be H.

2. A compound according to claim 1 of formula I and II wherein $R_3$ is $CH_3$.

3. A compound according to claim 2 of formula II wherein $R_3$ is $CH_3$.

4. A compound according to claim 3 wherein $R_1$ is H, $R_4$ is $-(CH_2)_2-NR_{4a}R_{4b}$, $R_{4a}$ and $R_{4b}$ are $CH_3$, and $R_6$ is $-(C_1-C_8)$alkoxy.

5. A compound according to claim 1 selected from the group consisting of:

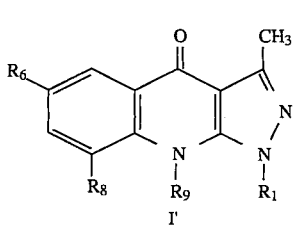
I'

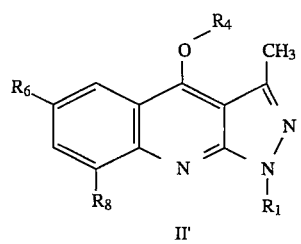
II'

| Compound, Formula | $R_6$ | $R_8$ | $R_4$ when Formula II', $R_9$ when Formula I' | $R_1$ |
|---|---|---|---|---|
| A, II' | OCOCH$_3$ | H | COCH$_3$ | H |
| B, II' | OCOCH$_3$ | H | H | COCH$_3$ |
| C, II' | OCOC$_4$H$_9$ | H | COC$_4$H$_9$ | H |
| D, II' | OCOC$_2$H$_5$ | H | COC$_2$H$_5$ | H |
| E, II' | OCH$_3$ | H | H | COCH$_3$ |
| F, II' | Cl | H | H | COCH$_3$ |
| G, II' | F | H | COCH$_3$ | H |
| H, II' | F | H | H | COCH$_3$ |
| I, II' | OCH$_3$ | H | COCH$_3$ | C$_7$H$_{15}$ |
| J, II' | CH$_3$ | H | H | COCH$_3$ |
| K, I' | OCH$_3$ | CH$_3$ | H | COCH$_3$ |
| L, I' | CH$_3$ | H | H | C$_7$H$_{15}$ |
| M, II' | CH$_3$ | H | COCH$_3$ | C$_7$H$_{15}$ |
| N, II' | H | OCH$_3$ | H | COCH$_3$ |
| O, II' | OCH$_3$ | H | $-CH_2CH_2N(CH_3)_2$ | H |
| P, II' | OCH$_3$ | H | CH$_3$ | $-(CH_2)_3OH$ |
| Q, II' | OCH$_3$ | H | $-(CH_2)_2$-N(morpholino) | H |

-continued

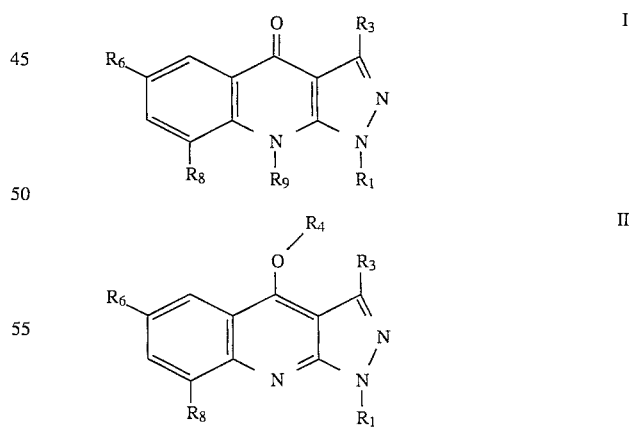

| Compound, Formula | $R_6$ | $R_8$ | $R_4$ when Formula II', $R_9$ when Formula I' | $R_1$ |
|---|---|---|---|---|
| R, II' | $OCH_2CH=CH_2$ | H | H | $-CH_2CH=CH_2$ |
| S, II' | $OCH_3$ | H | H | $C_7H_{15}$ |
| T, I' | H | $OCH_3$ | ⸦CH₂CH₂-O-C(=O)-C(CH₃)₃ | H |
| U, II' | H | $OCH_3$ | H | ⸦CH₂CH₂-O-C(=O)-C(CH₃)₃ |
| V, I' | H | $OCH_3$ | ⸦C(=O)-C(CH₃)₃ | H |
| W, II' | $OCH_3$ | H | H | ⸦C(=O)-O-CH₂-C₆H₅ |
| X, I' | $OCH_2CH=CH_2$ | H | $CH_2CH=CH_2$ | $CH_2CH=CH_2$ |
| NN, II' | $OCH_3$ | H | $CH_3$ | H | or a pharmaceutically acceptable salt thereof.

6. The compound according to claim 1 of the formula

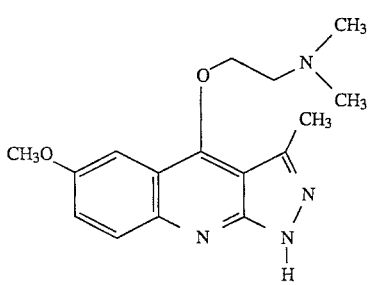

or a pharmaceutically acceptable salt thereof.

7. A pharmaceutical composition for treating patients afflicted with a herpes group virus which comprises an anti-herpes effective amount of a compound of formula I or II of claim 1 and a pharmaceutically acceptable carrier therefor.

8. A method of treating a patient afflicted with a herpes group virus which comprises administering to said patient an anti-herpes effective amount of a compound of formula I or II of claim 1.

9. A pharmaceutical composition for treating patients afflicted with a herpes group virus which comprises an anti-herpes effective amount of a compound of formula II of claim 1 and a pharmaceutically acceptable carrier therefor.

10. A method of treating a patient afflicted with a herpes group virus which comprises administering to said patient an anti-herpes effective amount of a compound of formula II of claim 1.

11. A compound of the formula I or II or a pharmaceutically acceptable salt thereof, wherein $R_1$ and $R_9$ each is independently H, $(C_1-C_8)$alkyl, $(C_1-C_8)$alkanoyl, $(C_1-C_5)$alkanoyloxymethyl, benzyloxycarbonyl, $(C_2-C_8)$alkenyl, or $(C_1-C_8)$hydroxyalkyl;

$R_3$ is H or $(C_1-C_3)$alkyl;

$R_4$ is H or $(C_1-C_5)$alkanoyl or $-(CH_2)_2-NR_{4a}R_{4b}$ where each $R_{4a}$ and $R_{4b}$ is independently H or ($C_1$–$C_8$)alkyl or $R_{4a}$ and $R_{4b}$ taken together are
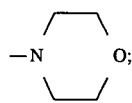
wherein $R_6$ and $R_8$ each is independently H, —O—($C_1$–$C_8$)alkanoyl, —($C_1$–$C_8$)alkoxy, ($C_2$–$C_8$)alkenyloxy or ($C_1$–$C_8$)alkyl;
with the proviso that when $R_1$ is H or —$CH_3$, $R_6$ is H or —$OCH_3$, and $R_9$ is H or —$CH_3$, then $R_3$ cannot be —$CH_3$;
and with the further proviso that when $R_4$ is ($C_1$–$C_8$)alkyl then $R_1$ must be H.
* * * * *